United States Patent [19]

Smith

[11] Patent Number: 5,285,791
[45] Date of Patent: Feb. 15, 1994

[54] NOISE DAMPING SYSTEM FOR AN AUTOMATIC BLOOD PRESSURE GAUGE

[75] Inventor: David L. Smith, Ipswich, Mass.

[73] Assignee: Siemens Medical Electronics, Inc., Danvers, Mass.

[21] Appl. No.: 823,735

[22] Filed: Jan. 21, 1992

[51] Int. Cl.$^5$ ............................................. A61B 5/00
[52] U.S. Cl. ........................................ 128/677; 128/680; 128/681
[58] Field of Search ........................... 128/680–686, 128/677, 672

[56] References Cited

U.S. PATENT DOCUMENTS

| | | | |
|---|---|---|---|
| 4,417,587 | 11/1983 | Ichinomiya et al. | 128/682 |
| 4,627,440 | 12/1986 | Ramsey et al. | 128/682 |
| 4,706,684 | 11/1987 | Sorensen et al. | 128/677 |
| 4,938,227 | 7/1990 | Niwa et al. | 128/680 |
| 5,092,338 | 3/1992 | Ide et al. | 128/677 |
| 5,099,851 | 3/1992 | Hata et al. | 128/680 |
| 5,143,077 | 9/1992 | Kobayashi | 128/680 |

Primary Examiner—Lee S. Cohen
Assistant Examiner—Robert L. Nasser, Sr.
Attorney, Agent, or Firm—Lawrence C. Edelman

[57] ABSTRACT

A noise damping system for use in connection with an automatic blood pressure measuring device. The system includes a manifold divided into two expansion chambers in fluid communication with one another by way of a chamber port. The pressure waves and acoustic noise generated by a pump and modulated valves are attenuated by expanding in one chamber against a resistance caused by the chamber port and by expansion in the second chamber against a resistance caused by a manifold inlet/outlet port leading to the ambient environment.

15 Claims, 8 Drawing Sheets

1

NOISE DAMPING SYSTEM FOR AN AUTOMATIC BLOOD PRESSURE GAUGE

FIELD OF THE INVENTION

The present invention pertains to apparatus for damping the noise created by pressure wave sources associated with systems for automatically monitoring the blood pressure of an individual.

BACKGROUND OF THE INVENTION

A conventional automatic blood pressure gauge includes a resilient inflatable cuff and an electric pump. The pump is controlled by a microprocessor to inflate the cuff with a fluid, such as air from the ambient environment, to a preset pressure. In addition, this automatic gauge includes a pressure transducer that measures the instantaneous air pressure levels in the cuff. The pressure signa) produced by the transducer is used to determine both the instantaneous air pressure of the cuff and the blood pressure pulse of the individual. This pressure signal is generally digitized and processed by the microprocessor to produce values representing the systolic and diastolic blood pressure measurements of the individual.

In operation, the cuff is affixed to the upper arm area of the patient and is then inflated to a pressure greater than the suspected systolic pressure, for example, 150 to 200 millimeters of mercury (mmHg). This pressure level collapses the main artery in the arm, effectively stopping any blood flow to the lower arm. Next, the cuff is deflated slowly and the transducer pressure signal is monitored to detect variations in cuff pressure caused by the patient's pulse, which is coupled into the cuff. By monitoring the amplitude of the measured pulse signal, the system can determine the patient's systolic and diastolic pressures.

One exemplary system is described in U.S. Pat. No. 4,949,710 entitled METHOD OF ARTIFACT REJECTION FOR NONINVASIVE BLOOD-PRESSURE MEASUREMENT BY PREDICTION AND ADJUSTMENT OF BLOOD-PRESSURE DATA, which is hereby incorporated by reference for its teaching on automatic blood pressure gauges. This system monitors the patient's blood pressure signal to determine the maximum detected pulse amplitude. This is commonly referred to as the mean arterial pressure (MAP). The systolic and diastolic blood pressure levels are then determined as the respective pressures corresponding to the amplitude of the pulse signal being 60% of the maximum value, prior to reaching the maximum value; and 80% of the maximum value, after reaching the maximum value.

To be most effective, an automatic blood pressure gauge should quickly inflate the cuff to a preset pressure value and then deflate the cuff according to a known deflation curve. It is desirable to complete this task in a relatively short time period, so as to provide quick results and to minimize patient anxiety and discomfort.

The pump, described above, permits quick inflation and one or more valves permit deflation. However, these pumps and valves are likely to cause pressure waves and acoustic noise. The pressure waves could propagate through the system, be detected by the pressure transducer and, so, interfere with the detection of the pulse data. In addition, the acoustic noise tends to be an annoyance for the user and the patient, especially if the measurement system is used over long periods of time or frequently used.

One exemplary system for decreasing the noise of a blood pressure monitoring system is described in U.S. Pat. No. 4,949,710 entitled LINEAR, LOW NOISE INFLATION SYSTEM FOR BLOOD PRESSURE MONITOR. This system uses two acoustic filters, one coupled to the inlet side of a pump for inflating a cuff and the other coupled to the outlet side of the pump. The pressure waves produced by the pump are propagated through longitudinal bores in the acoustic filters, then attenuated in resonance chambers coupled to the longitudinal bores by Way of transverse bores.

SUMMARY OF THE INVENTION

The present invention is a manifold for use in connection with a blood pressure monitoring device having a cuff and a pump. The manifold is adapted to provide fluid flow to the pump and from the pump to the cuff during cuff inflation, and is adapted to provide fluid flow from the cuff during cuff deflation. The manifold includes a noise damping chamber for damping pressure waves during inflation and deflation of the cuff.

According to another aspect of the invention, the manifold includes a partition defining first and second expansion chambers, in direct fluid communication with one another, for damping pressure waves. Fluid flow is provided from the first expansion chamber to the pump, and fluid flow is also provided between the cuff and the first and second expansion chambers.

According to another aspect of the invention, the blood pressure monitoring system includes first and second modulated valves which create pressure waves during cuff deflation. The first modulated valve is in direct fluid communication with the first expansion chamber and produces pressure waves, which are attenuated through both the first and second expansion chambers; the second modulated valve is in direct fluid communication with the second expansion chamber, and its pressure waves are attenuated through the second expansion chamber.

According to another aspect of the invention, a first debris filter is positioned between the manifold and the cuff and a second debris filter is positioned between the manifold and the ambient atmosphere.

DETAILED DESCRIPTION OF THE INVENTION

Prior to a discussion of the noise damping system and manifold of the present invention and its operation, it is helpful to discuss a blood pressure monitoring system in which the present invention may be used.

Figure 1:
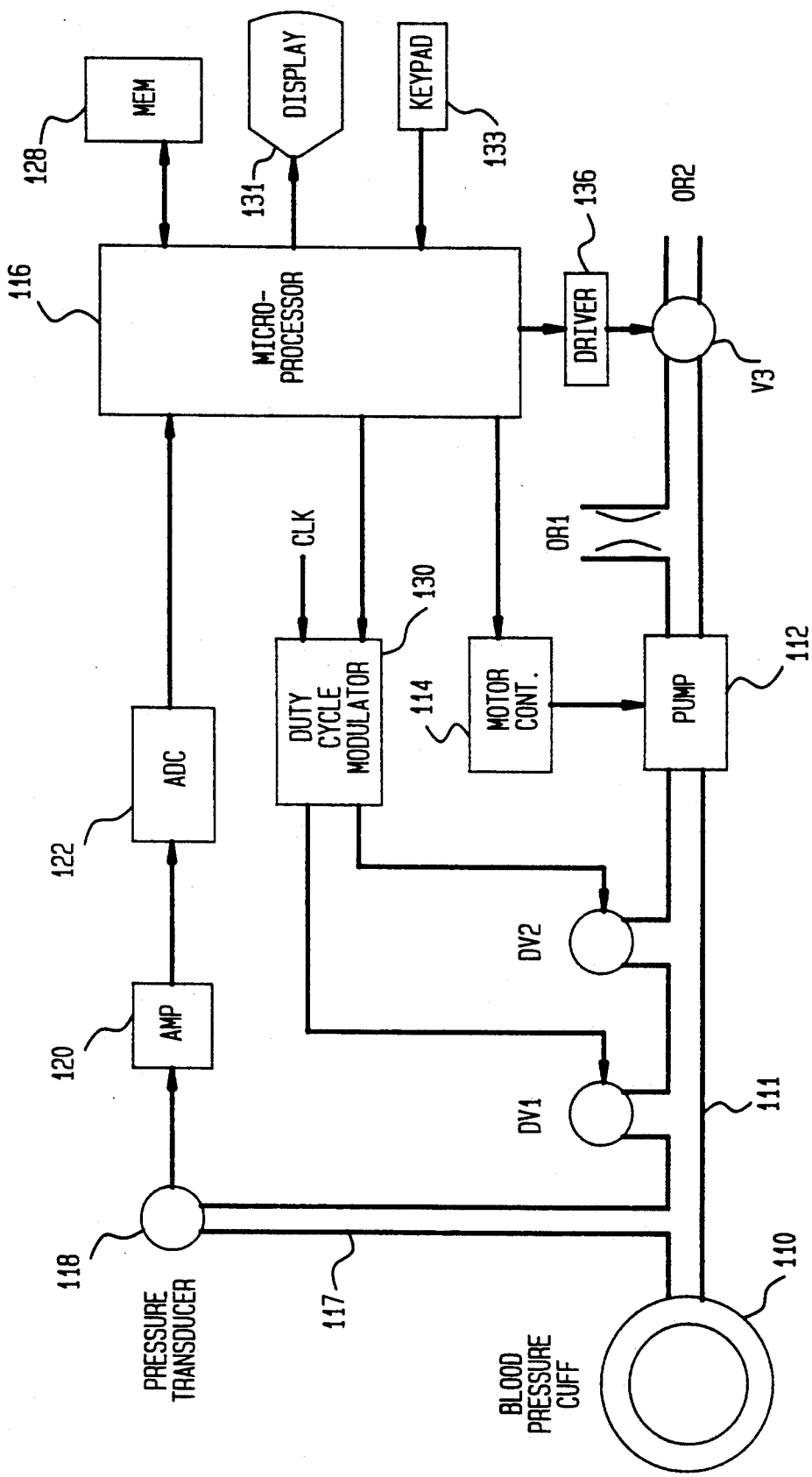
FIG. 1 is a block diagram of an automatic blood pressure measurement system Which shows an environment in which the present invention may be used.

FIG. 1 is a block diagram of such an exemplary blood pressure monitoring system 100. This system includes a conventional blood pressure cuff 110 which may be inflated by an electric pump 112 using an air channel 111. The pump motor is turned on and off by a motor controller 114 which is responsive to signals provided by a microprocessor 116. A suitable pump for use in this embodiment of invention is a diaphragm type, driven by a low inertia DC motor.

Air is supplied to the pump 112 through an orifice, OR1 which has a restricted flow and through an orifice, OR2 which, although unrestricted, may be selectively blocked by closing a solenoid valve V3 in series with the orifice OR2 and the intake port of the pump 112. The inflation valve V3 is controlled by the microprocessor 116 via driver circuitry 136 as described below.

The cuff is deflated using two controlled solenoid valves, DV1 and DV2. When open, the valve DV1 may have a relatively low flow rate, and the valve DV2 may have a relatively high flow rate. For example, the valve DV1 may have a flow rate of 570 standard milliliters per minute (Std ml/min) at 170 mmHg differential pressure, and the valve DV2 may have a flow rate of 1,341 Std ml/min at 20 mmHg differential pressure. These valves may be opened and closed in 1.4 milliseconds (ms) and 6 ms, respectively. In this embodiment of the invention, the valves are controlled by a pulse-width modulated signal having a set nominal frequency. Only one of the valves is open at any given time during normal operation. By controlling the percentage of time that the valve is opened and closed within each cycle of the control signal, the time-aperture of the valve can be effectively controlled. This time-aperture determines the average rate of airflow through the valve. Opening and closing the valves also produces undesirable pressure waves.

The microprocessor 116 controls the valves DV1 and DV2 using a duty cycle modulator 130. The modulator 130 produces a variable duty cycle oscillatory signal which controls a selected one of the valves DV1 and DV2. The duty cycle of this signal is controlled to determine the effective aperture of the selected valve, and thus, the rate at which the cuff 110 is deflated.

The microprocessor 116 monitors the air pressure in the cuff using a conventional pressure transducer 118 which is coupled to the air channel 111 via a tube 117. In the exemplary embodiment of the invention, the pressure transducer is of the conventional semiconductor strain gauge type. The signal produced by the transducer 118 is amplified by a low-noise instrument quality amplifier 120 which produces a signal that is applied to an analog to digital converter (ADC) 122. In this embodiment of the invention, the ADC 122 is a 16-bit sigma-delta type analog to digital converter. The ADC 122 produces samples at a rate of approximately 50 Hz.

The sampled data pressure signal provided by the ADC 122 is monitored by the microprocessor 116 to start the pump when a pressure measurement has been requested; to stop the pump 112 when the desired initial cuff pressure has been obtained; to control the flow through the deflation valves DV1 and DV2; and to extract, from the pulse signal, the systolic and diastolic blood pressure measurements for the individual.

The blood pressure measurements are presented to the operator on a display device 131. To produce these values, the microprocessor 116 operates under the control of a program stored in the memory 128. The memory 128 also contains cells which may be used for storing temporary data values. In the exemplary embodiment of the invention, the program storage portion of the memory 128 is a read-only memory (ROM) while the data storage portion is a random-access memory (RAM). Operator commands to the blood pressure gauge are provided to the microprocessor 116 via a keypad 133.

The microprocessor 116 captures samples produced by the ADC 122 at a 50 Hz rate. The collected samples are processed in groups of 45 to obtain a noise-reduced cuff pressure signal and its first derivative, representing the actual rate of change of the cuff pressure. These signals have an effective sampling rate of 1.11 Hz. While the cuff 110 is being inflated, the microprocessor 116 determines if the pump 112 should be stopped for each sample of this signal. While the cuff is being deflated, the microprocessor 116 uses this signal to calculate new settings for the deflation valve DV1 or DV2. The microprocessor 116 controls the deflation valves DV1 and DV2, through the duty cycle modulator 130 to release fluid from the cuff at a constant rate in order to achieve a linear reduction in cuff pressure.

Referring to FIG. 1, when the operator indicates, via the keypad 133, that the cuff 110 is a neonatal cuff, the microprocessor 116 applies a signal to the driver 136 causing it to close the inflation valve V3. In this configuration, restricted orifice OR1 is the only source of air for the pump 112. Using only the restricted orifice OR1, neonatal cuffs inflate in 1 to 8 seconds.

When the operator indicates that the cuff 110 is o a pediatric or adult cuff, the microprocessor 116 conditions the driver 136 to open the valve V3. This increases the pump flow approximately by a factor of five. With both valves open the smallest pediatric cuffs inflate in about 1 second and the largest adult cuffs inflate in about 10 seconds.

The above blood pressure monitoring system 100 is one exemplary system in which the manifold and noise damping system of the present invention may be used. The manifold of the present invention may define one noise damping chamber, or pressure wave expansion chamber.

Figure 2:
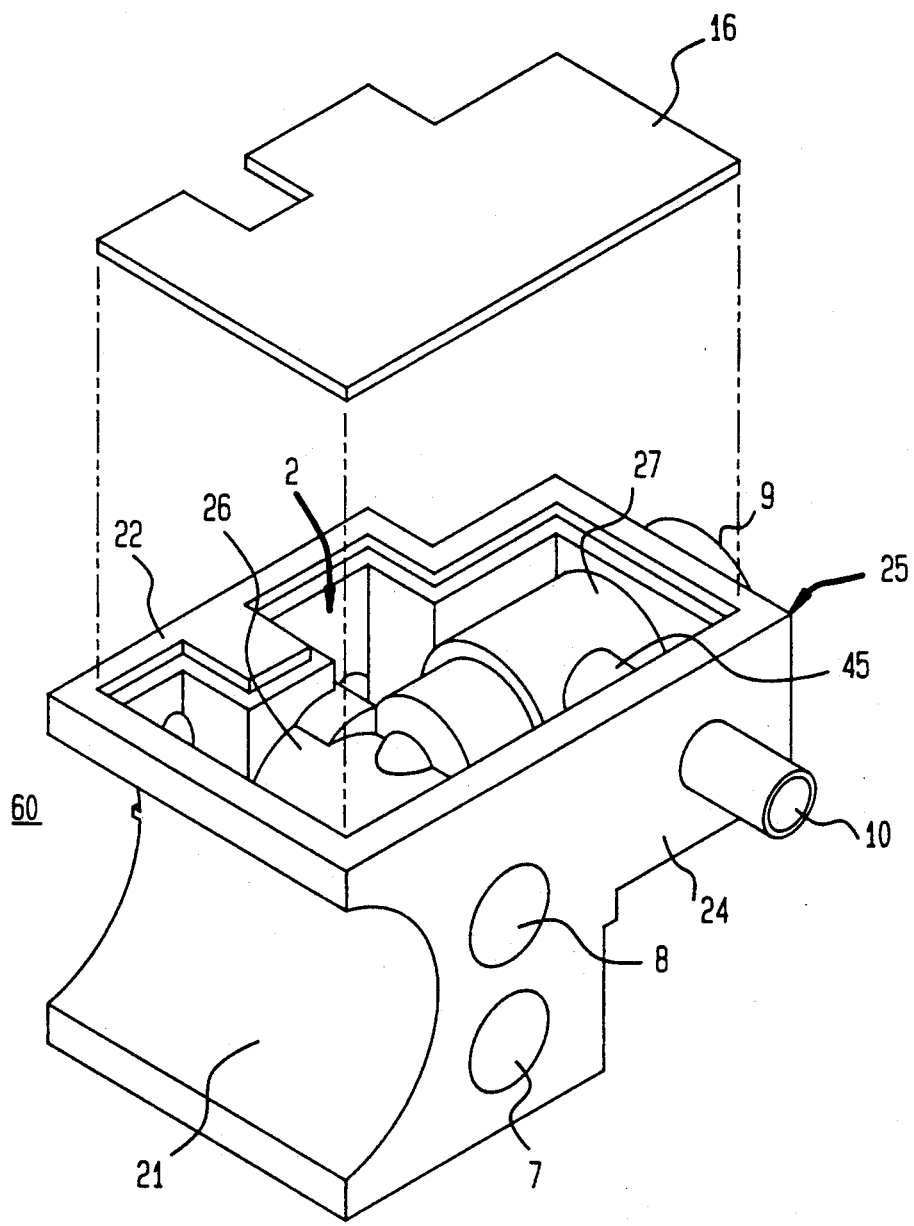
FIG. 2 is a perspective view, partially cut away, of a manifold which includes an embodiment of the present invention showing portions of the interior of the lower expansion chamber.

A manifold 60 having an expansion chamber 2 is shown in FIG. 2. Fluid is provided from a manifold port (not shown in FIG. 2) through the expansion chamber 2 to the pump by means of pump inlet port 7. The pump may be mounted on manifold 60 at side wall 24. Fluid from the pump flows through pump outlet port 8, through conduit 26, 27 and 45 and to cuff port 10 leading to a cuff. During deflation of the cuff, fluid flows from the cuff and through conduits 45 and 27 in a direction opposite to the direction of flow during inflation. In this way, manifold 60 permits bi-directional flow.

Pressure waves are produced by the pump during inflation of the cuff and by other sources during deflation of the cuff. These pressure waves are attenuated by expanding within chamber 2 against a resistance created by the manifold port (not shown in FIG. 2) to the ambient atmosphere. In this way, the acoustic noise associated with the pressure waves is effectively muffled. The flow of the fluid is similar to the fluid flow when the manifold defines two expansion chambers, discussed in more detail below.

Figure 3:
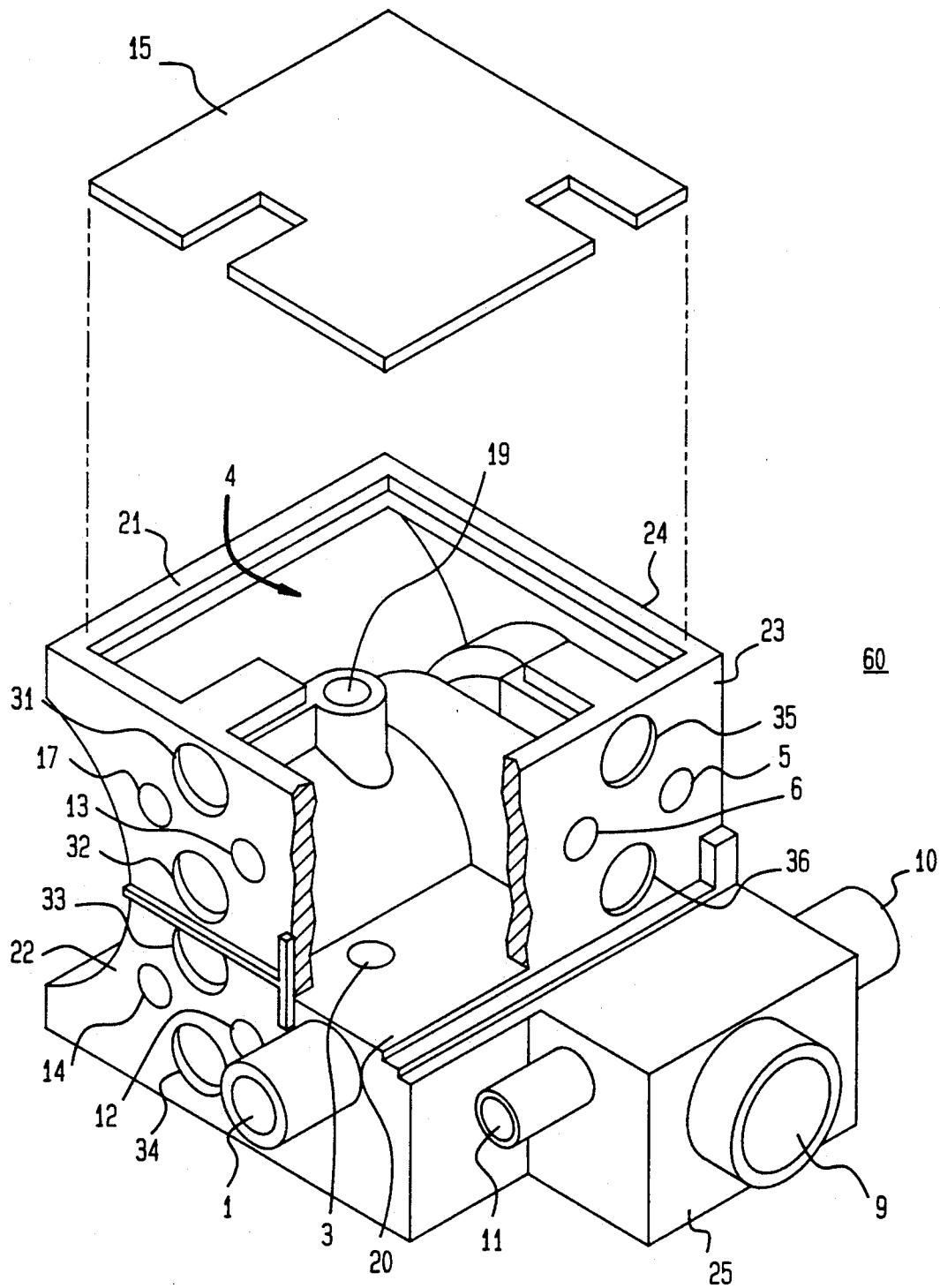
FIG. 3 is a perspective view of the manifold shown in FIG. 2, showing portions of the interior of the upper expansion chamber.

According to another embodiment of the invention, manifold 60 includes a partition defining an upper and a lower expansion chamber. This partition 20 is shown in FIG. 3, but not shown in FIG. 2. It is to be understood that for purposes of this embodiment, the chamber shown in FIG. 2 is one of two chambers of the manifold; in the first embodiment, the chamber shown in FIG. 2 was the only chamber of the manifold.

As shown in FIGS. 2 and 3, the noise damping system of this embodiment comprises a manifold defining two chambers, upper expansion chamber 4 and lower expansion chamber 2, each of which has several ports and conduits. The manifold shown in FIGS. 2 and 3 both interconnects the pump and valves, and acts as a muffler to dampen the pressure waves and associated acoustic noise generated by the pump and valves.

As shown in FIG. 3, the interior of manifold 60 is in fluid communication with the ambient environment by means of manifold port 1, to which a hose 18 (shown in FIG. 4) may be attached. This manifold port 1 is in fluid communication directly with lower expansion chamber 2 and indirectly with upper expansion chamber 4 by way of chamber port 3. Chamber port 3 is an opening in a partition 20, which divides upper expansion chamber 4 and lower expansion chamber 2 and provides direct fluid communication between the two expansion chambers.

As shown in FIG. 3, the interior of upper expansion chamber 4 is confined by convex rear wall 21, side walls 22 and 24, front wall 23, and partition 20. In operation, top cover 15 is in place, covering hole 19 and sealing the expansion chamber.

Similarly, as shown in FIG. 2, the interior of expansion chamber 2 is confined by convex rear wall 21, side walls 22 and 24, partition 20 (not shown in FIG. 2), and protrusion 25. In operation, bottom cover 16 is sealed into place. Top cover 15 and bottom cover 16 may be ultrasonically welded in place to form an air-tight seal at 10 psi. No flashing or other debris should be allowed inside the manifold during this welding process.

Referring to FIG. 3, wall 22 includes two ports 13 and 17, which may be inlet and outlet ports, respectively, of a deflation valve, such as deflation valve DV1 as discussed in FIG. 1. Also, the lower portion of wall 22 includes ports 12 and 14, which are inlet and outlet ports, respectively, of a deflation valve, such as deflation valve DV2 as discussed in FIG. 1. Additionally, front wall 23 includes two ports 5 and 6, which are inlet and outlet ports, respectively, of an inflation valve, such as valve V3, as shown in FIG. 1.

Adjacent each set of inlet and outlet ports are a pair of mounting openings for the valves. Adjacent ports 13 and 17 are mounting openings 31 and 32 to mount deflation valve DV1. Adjacent ports 12 and 14 are mounting openings 33 and 34 to mount deflation valve DV2. Adjacent ports 5 and 6 are mounting openings 35 and 36 to mount valve V3. Associated with each mounting opening is a device for coupling the valves to manifold 60. For example, the mounting openings could be threaded to receive screws for mounting the valves.

Protrusion 25 extends outwardly from manifold 60. Protrusion 25 includes a pressure sensor port 11, a debris filter 9 and a cuff port 10. Pressure sensor port 11 may lead to a pressure transducer 118, for measuring pressure, as discussed in reference to FIG. 1. Cuff port 10 may be attached to a hose (not shown) leading to the cuff for pressurizing the cuff 110, as shown in FIG. 1.

FIG. 2 shows the interior of the lower expansion chamber 2. A more complete view of convex rear wall 21 and side wall 24 is shown than in FIG. 3. Side wall 24 includes two ports 7 and 8, which are the inlet and outlet ports for a pump, such as pump 112 as discussed in reference to FIG. 1.

The entire manifold as shown may be approximately one cubic inch in volume. As such, each expansion chamber may be less than one cubic inch in volume. The material used may be any of a number of plastics.

Figure 4:
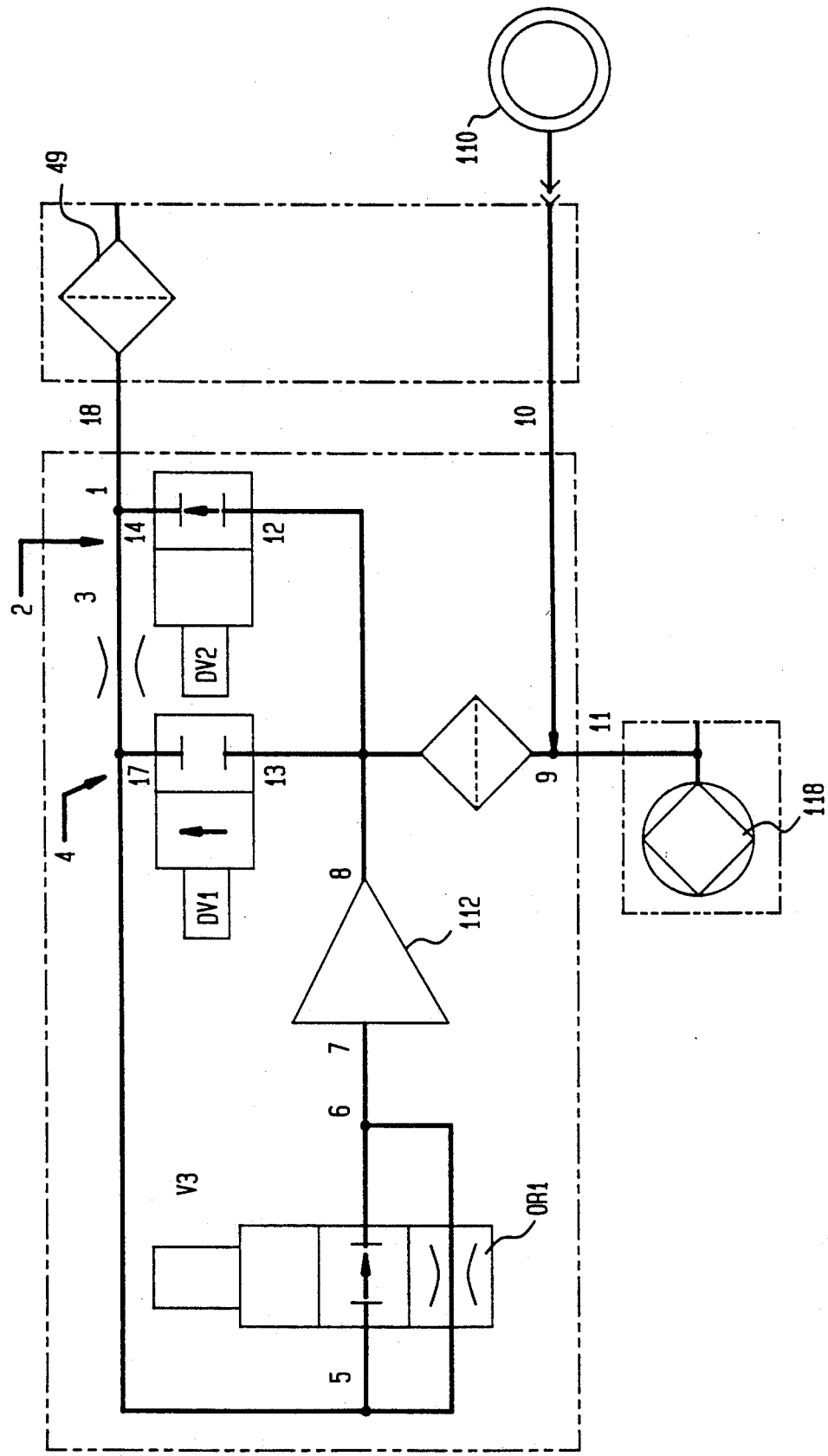
FIG. 4 is a functional block diagram of the manifold shown in FIGS. 2 and 3.

FIG. 4 is a functional block diagram which is useful for discussing the operation of the noise reduction system of the present invention. During inflation, pump 112 operates to draw fluid through an ambient filter 49, then through hose 18 and port 1, and then into lower expansion chamber 2. This fluid then flows through chamber port 3 and into upper expansion chamber 4. Fluid flows from expansion chamber 4 through port 5 into valve V3 which is mounted on manifold 60 and in fluid communication with upper expansion chamber 4 and which includes restricted orifice OR1.

Figure 5A:
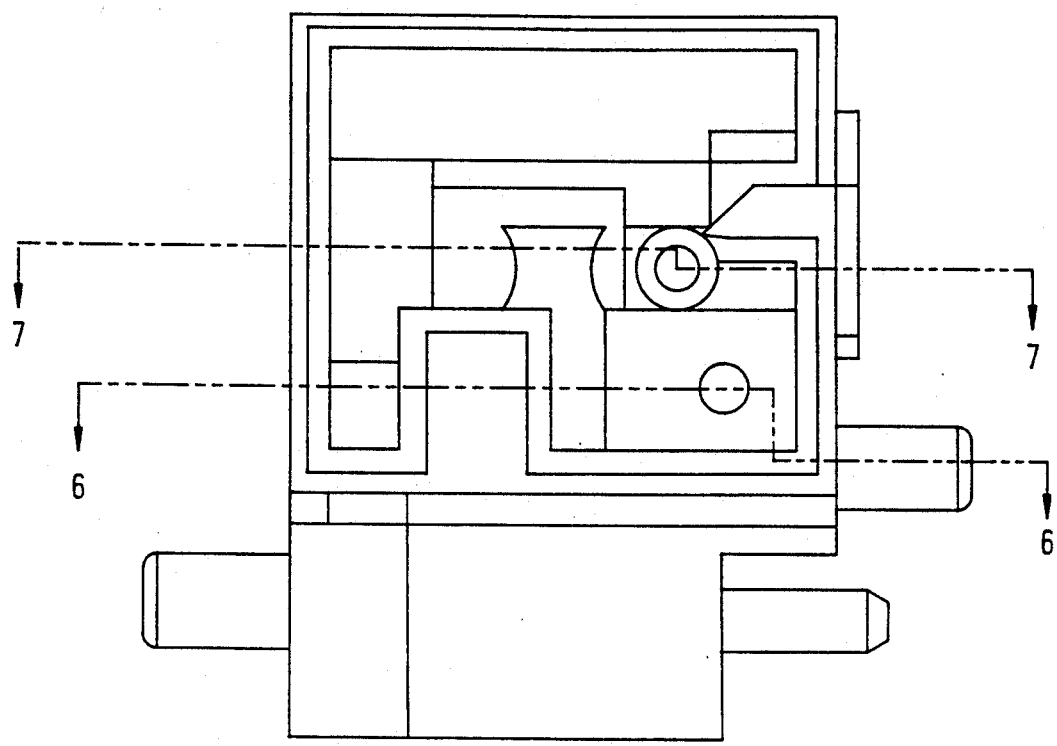
FIGS. 5a, 5b and 5c are top, front and bottom plan views, respectively, of the manifold shown in FIGS. 2 and 3.
Figure 5B:
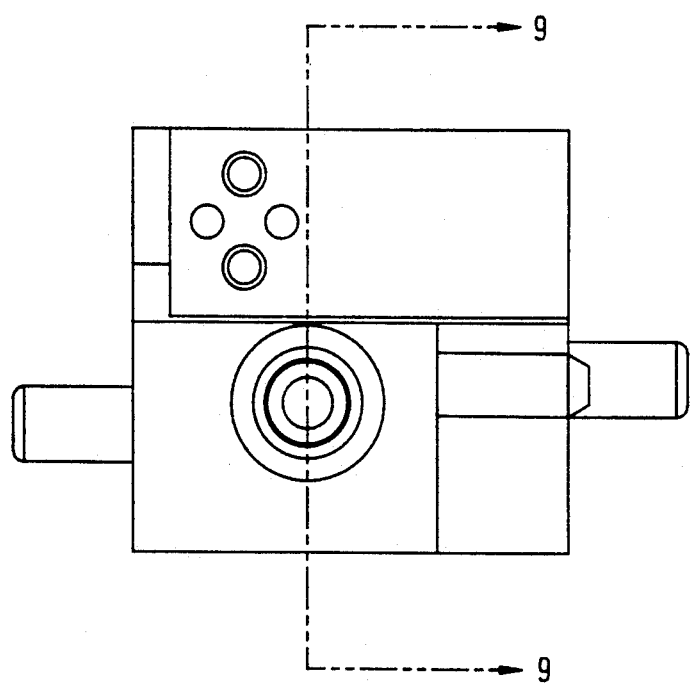
Figure 5C:
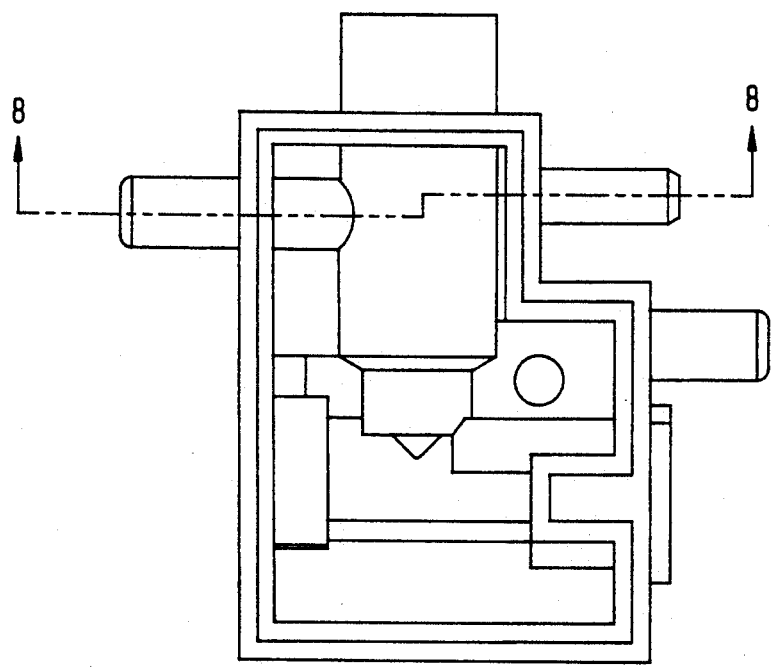
Figure 6:
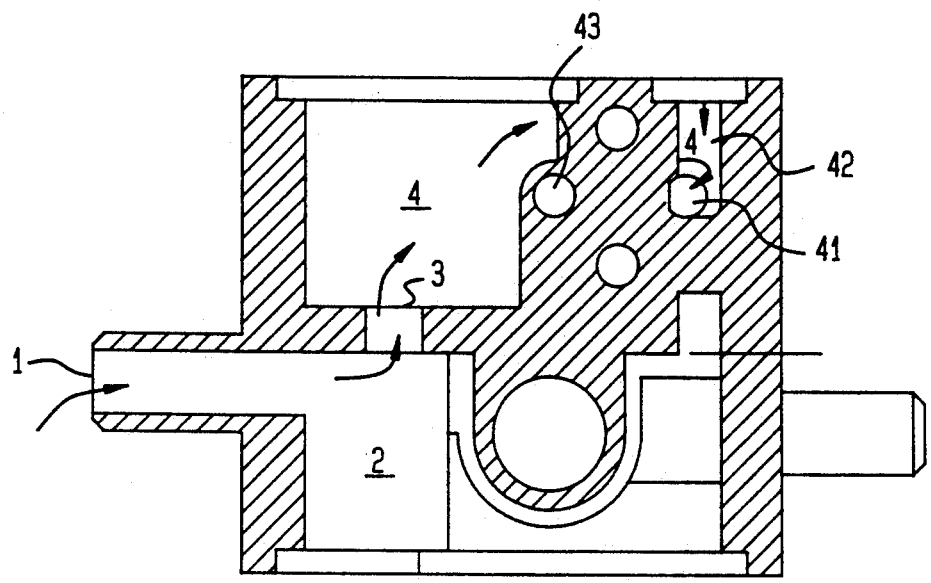
FIGS. 6–9 are cross section diagrams of the manifold shown in FIGS. 2 and 3, taken along the lines indicated in FIGS. 5a, 5b and 5c.

The flow path of the fluid during inflation may also be shown using the cross-sectional FIGS. 6–9, which are taken along the lines shown in FIGS. 5a, 5b and 5c. Referring to FIG. 6, the fluid flow path during inflation is in the direction of the arrows shown. The pump draws fluid from the ambient environment through manifold port 1, into lower expansion chamber 2, through chamber port 3 into upper expansion chamber 4. Fluid flows from expansion chamber 4 in the direction indicated by arrows 42. Conduit 41 is the extension of inlet port 5 of inflation valve V3.

Figure 7:
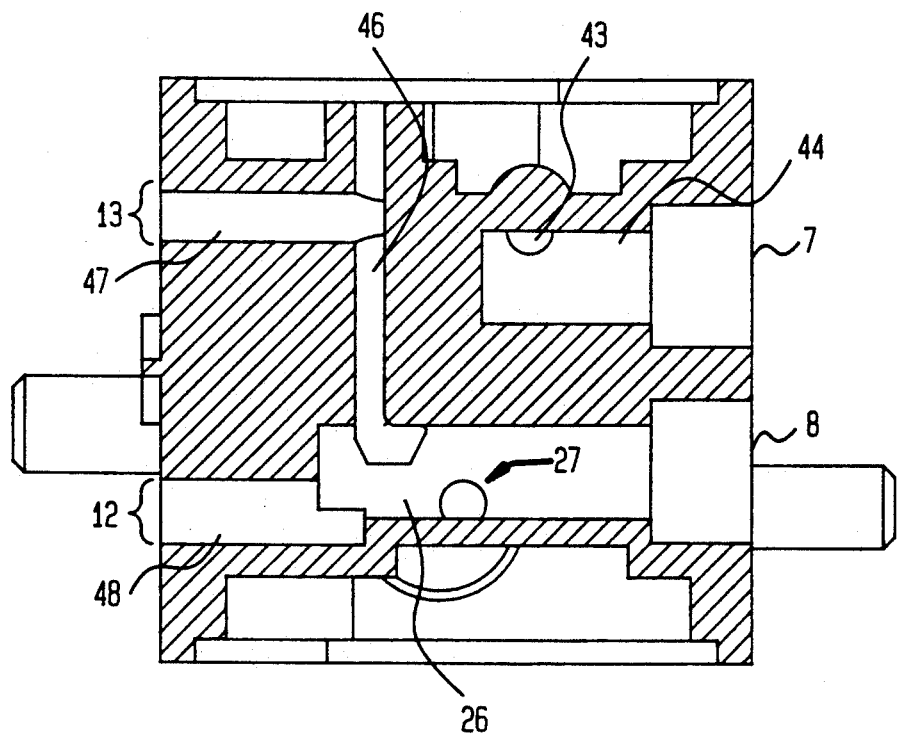

After passing through valve V3, the fluid re-enters manifold 60 through port 6 (shown in FIG. 3) and into conduit 43. As shown in FIG. 7, conduit 43 is in fluid flow communication with pump inlet conduit 44, which leads to pump inlet port 7.

Figure 8:
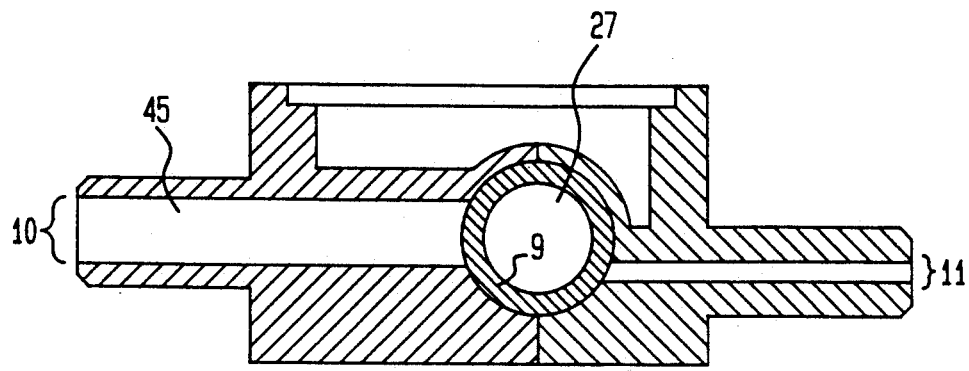
Figure 9:
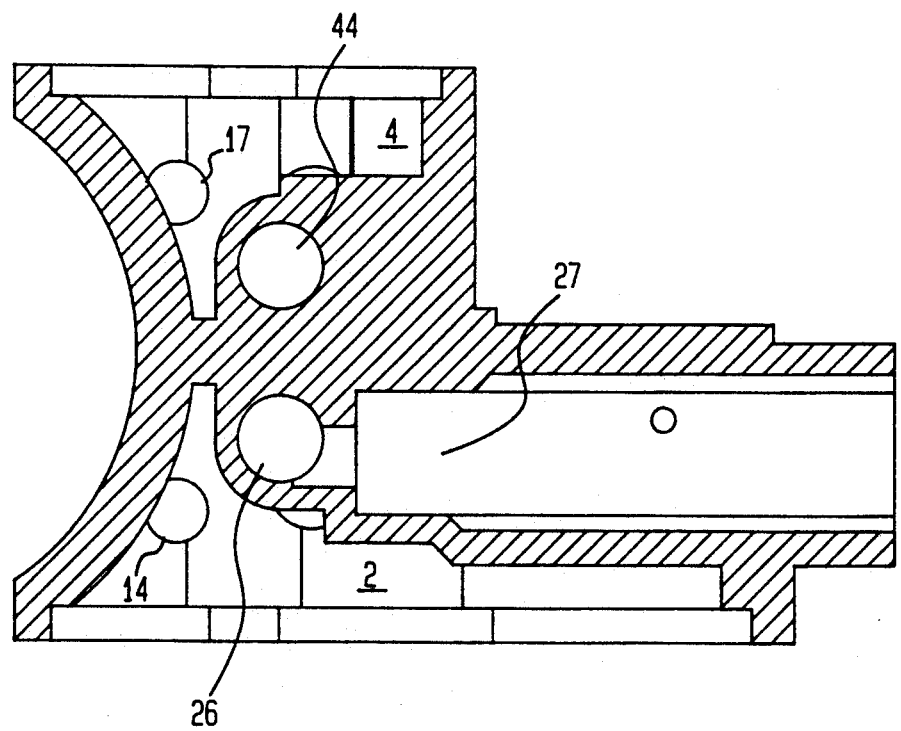

The draw to pump 112 is complete at pump input port 7 of wall 24 (shown in FIG. 2) of upper expansion chamber 4. From pump 112, the fluid is pressurized and enters conduit 26 through pump output port 8 as shown in FIGS. 3 and 7. Conduit 26 is in fluid communication with and flows perpendicular to conduit 27, which contains filter 9. As shown in FIG. 8, from conduit 27, the pressurized fluid flows across filter 9 through cuff port 10 then to the cuff. The flow path from the pump outlet is also shown in FIGS. 8 and 9. In the view shown in FIG. 9, the filter 9 has been removed. As shown, conduit 27 is in fluid communication with cuff conduit 45 leading to cuff port 10. Port 11 is in fluid communication with pressure transducer 118, as shown in FIGS. 4 and 8.

Deflation of the cuff can occur through either deflation valve DV1 or deflation valve DV2. During measurement, a relatively small flow rate is desired. Therefore, when the cuff pressure is relatively high, it is advantageous to permit fluid to flow through deflation valve DV1 because deflation valve DV1 permits a much lower flow rate than that of deflation valve DV2.

During measurement, the cuff is deflated by permitting fluid to flow through cuff port 10 and into conduit 27, again crossing filter 9. This bi-directional flow across the filter during inflation and deflation is advantageous, permitting cleaning of the filter during operation. In other words, during deflation of the cuff, filter 9 prevents debris from entering the manifold from the cuff. During inflation of the cuff, the debris caught in filter 9 is purged from the filter into the cuff. Periodically, the pump may be operated with cuff port 10 connected to a hose leading to a waste container, instead of a cuff, in order to clean the filter removing any debris from the system.

When deflation valve DV1 is selected, the fluid, after flowing across filter 9, reaches port 13 of the deflation valve DV1 by flowing through conduits 46 and 47 as shown in FIG. 7. The fluid then flows through the selected pulse modulated deflation valve DV1 and into upper expansion chamber 4 through port 17, as shown in FIG. 9. From upper expansion chamber 4, the fluid passes through chamber port 3, and into lower expansion chamber 2 and out manifold port 1. From port 1, the fluid flows through hose 18, through ambient filter 49 (shown in FIG. 4) and to the ambient environment.

The bi-directional flow of the system advantageously removes debris trapped in filter 49, similar to the process to remove debris from filter 9. For example, during inflation of the cuff, fluid from the ambient environment is pulled across filter 49 by the pump. The ambient environment may include debris which is trapped in filter 49. During deflation of the cuff, this debris is purged from filter 49 because of the reverse direction of the fluid flow.

The pressure waves and acoustic noise created by the pulsating action of modulated deflation valve DV1 are first attenuated in upper expansion chamber 4 against a resistance cause by chamber port 3. These pressure waves are further attenuated by the expansion in lower expansion chamber 2 and against a resistance caused by manifold port 1 and hose 18 (shown in FIG. 4).

Deflation valve DV2, which permits a much greater fluid flow rate, can be used during deflation when the cuff pressure is relatively low or after measurement to permit full rapid deflation. From the cuff to conduit 27, there is a similar flow rate as when the cuff is being deflated by deflation valve DV1. From conduit 27, the fluid reaches inlet port 12 to deflation valve DV2 by flowing through conduit 48, as shown in FIG. 7. The fluid then flows through pulse modulated deflation valve DV2, through deflation valve outlet port 14 and into lower expansion chamber 2, as shown in FIG. 9. The pressure waves caused by modulating deflation valve DV1 are muffled by expansion in expansion chamber 2 against a resistance caused by port 1 and hose 18. In this way, the acoustic noise associated with these pressure waves are muffled.

The configuration of having deflation valve DV1 coupled to upper expansion chamber 4 and deflation valve DV2 coupled to lower expansion chamber 2 is also particularly advantageous because less resistance is presented to the higher flow rate deflation valve DV2. Also, if one valve produces significantly larger pressure waves than another, it is preferred to subject the significantly larger pressure waves to two expansion chambers in order to ensure maximal attenuation of sound waves.

Furthermore, pressure waves and acoustic noise caused by the pump 112 are attenuated first by expansion in chamber 4 against the resistance of chamber port 3, and then by the expansion in lower expansion chamber 2 against the resistance caused by port 1 and hose 18.

Thus, there has been shown and described a novel manifold for use in a blood pressure monitoring device which fulfills all the objects and advantages thereof. Many changes, modifications, variations and other uses and applications of the subject invention will, however, become apparent to those skilled in the art after considering this specification and its accompanying drawings which disclose preferred embodiments thereof. All such changes, modifications, variations and other uses and applications which do not depart from the spirit and scope of the invention and deemed to be covered by the invention which is limited only by the claims which follow.

What is claimed:

1. A blood pressure monitoring system having a cuff, a deflation valve, a pump, and a manifold, said manifold comprising:
    a partition defining a first expansion chamber and a second expansion chamber for damping fluid pressure waves, wherein said partition includes a first flow resistrictor for providing direct fluid communication between said first expansion chamber and said second expansion chamber;
    inflation path means for providing fluid flow from an ambient source of said fluid to at least one of said first and second expansion chambers, and then to said pump and said cuff, in the named order, for inflating said cuff with fluid; and
    deflation path means for providing fluid flow from said cuff to said deflation valve and then to at least one of said first and second expansion chambers, in said named order, for deflating said cuff of fluid;
    wherein at least one of said inflation path means and said deflation path means provides said fluid flow using both of said first and second expansion chambers with said first flow restrictor therebetween.

2. A system in accordance with claim 1 wherein the first flow resistrictor is a chamber port, which creates a resistance against which said fluid pressure waves propagated through said first expansion chamber are damped.

3. A system in accordance with claim 2 wherein said second expansion chamber includes a second flow resistrictor as a manifold port, which provides fluid communication with said ambient fluid source, the manifold port creating a resistance against which said fluid pressure waves propagated through said second expansion chamber are damped as they flow between said second expansion chamber and said ambient source of fluid.

4. A system in accordance with claim 3 wherein said system includes a hose, coupled to said manifold near said manifold port, which conveys fluid between the ambient environment and said manifold.

5. A system in accordance with claim 3, wherein:
    said second expansion chamber is common to both said inflation and deflation path means; and
    a debris filter is coupled to said second expansion chamber and adapted to be coupled to said ambient source.

6. A system in accordance with claim 1 wherein:
    a first modulated deflation valve is coupled to said manifold and includes a valve inlet port which provides fluid communication with said cuff and a valve outlet port which is in fluid communication with said first expansion chamber for deflating said cuff using a portion of said deflation path means which includes said first expansion chamber, said first flow restrictor and said second expansion chamber; and, a second modulated deflation valve is coupled to said manifold, and includes a valve inlet port which provides fluid communication with said cuff and a valve outlet port which is in fluid communication with said second expansion chamber for deflating said cuff using a portion of the deflation path means which includes said second expansion chamber but does not include said first expansion chamber or said first flow restrictor.

7. A system in accordance with claim 1 wherein said first and said second expansion chambers are each less than one cubic inch in volume.

8. A system in accordance with claim 1, wherein:
both said inflation path means and said deflation path means provide fluid flow using the first and second expansion chambers and said first flow restrictor.

9. A system in accordance with claim 8, wherein:
a debris filter is coupled to said second expansion chamber and is adapted to be coupled to said ambient source.

10. A low acoustic noise blood pressure monitoring system using a cuff, said system comprising:
a pump for inflating said cuff from an ambient atmosphere;
a first modulated deflation valve and a second modulated deflation valve for deflating said cuff into the ambient atmosphere; and
a manifold having means for providing fluid flow in a first direction to said pump and from said pump to said cuff during inflation of said cuff, and having means for providing fluid flow in a second direction, substantially opposite said first direction, from said cuff during deflation of said cuff, and having a noise damping flow path including first and second series connected expansion chambers having a fluid flow restrictor providing a direct fluid coupling therebetween;
wherein one of said first and second modulated deflation valves is coupled to said noise damping flow path so as to provide deflation of said cuff to said ambient atmosphere during a measurment phase of operation for said blood pressure monitoring system via both said first and second series connected expansion chambers, and the other of said first and second modulated deflation valves is coupled to said noise damping flow path so as to deflate said cuff via only one of said series connected expansion chambers to said ambient atmosphere.

11. A low noise blood pressure monitoring system in accordance with claim 10 wherein said system includes a first debris filter positioned to filter the fluid flowing between said manifold and said cuff and a second debris filter positioned to filter the fluid flowing between said manifold and the ambient atmosphere.

12. A low noise blood pressure monitoring system in accordance with claim 10, wherein:
said noise damping flow path includes, as a further flow restrictor, a manifold port, in fluid communication with the ambient atmosphere, which creates a resistance against which said pressure waves propagated through said second expansion chamber are damped.

13. A low noise blood pressure monitoring system in accordance with claim 10, wherein:
a debris filter is coupled to said second expansion chamber and is adapted to be coupled to said ambient atmosphere.

14. A low noise blood pressure monitoring system in accordance with claim 10, wherein:
said first and second modulated deflation valves are solenoid valves having time-apertures which may be changed in response to a control signal, for venting the fluid from said cuff to said ambient atmosphere at a rate determined by the value of said control signal, said first modulated valve being operated so as to have relatively small time apertures during the measurement phase of operation for said monitoring system and being coupled to said noise damping flow path so as to deflate via said first and second expansion chambers, and said second modulated deflation valve having a time aperture so as to cause a relatively fast deflation rate of said cuff to said ambient atmosphere via only said second one of said first and second expansion chambers of the noise damping flow path.

15. A low noise blood pressure monitoring system in accordance with claim 10, wherein:
said fluid flow provided by said manifold in said first and second directions provide fluid flow between both of said first and second expansion chambers.

* * * * *